(12) United States Patent
Schmidt et al.

(10) Patent No.: US 7,297,379 B2
(45) Date of Patent: Nov. 20, 2007

(54) POLYFLUORINATED FUSED AROMATICS AND THEIR USE IN LIQUID-CRYSTAL MIXTURES

(75) Inventors: Wolfgang Schmidt, Dreieich (DE); Rainer Wingen, Hofheim (DE); Barbara Hornung, Hasselroth (DE)

(73) Assignee: Merck Patent GmbH, Darmstadt (DE)

( * ) Notice: Subject to any disclaimer, the term of this patent is extended or adjusted under 35 U.S.C. 154(b) by 114 days.

(21) Appl. No.: 11/127,999

(22) Filed: May 12, 2005

(65) Prior Publication Data

US 2005/0255258 A1 Nov. 17, 2005

(30) Foreign Application Priority Data

May 13, 2004 (DE) .............. 10 2004 023 914

(51) Int. Cl.
*C09K 19/32* (2006.01)
*C07C 23/40* (2006.01)

(52) U.S. Cl. .................. 428/1.1; 252/299.62; 570/183; 570/187

(58) Field of Classification Search ............... 428/1.1; 252/299.62, 299.01; 570/183, 187
See application file for complete search history.

(56) References Cited

U.S. PATENT DOCUMENTS

| | | | |
|---|---|---|---|
| 5,648,021 A | | 7/1997 | Wingen et al. |
| 5,888,422 A | | 3/1999 | Manero et al. |
| 6,168,838 B1 | | 1/2001 | Schmidt et al. |
| 6,558,758 B1 | | 5/2003 | Yanai et al. |
| 7,018,685 B2 | * | 3/2006 | Schmidt et al. ............ 428/1.1 |
| 7,067,179 B1 | * | 6/2006 | Ogawa et al. ............ 428/1.1 |
| 7,087,272 B2 | * | 8/2006 | Bremer et al. ............ 428/1.1 |
| 2004/0106798 A1 | | 6/2004 | Bremer et al. |
| 2004/0124399 A1 | | 7/2004 | Schmidt et al. |

FOREIGN PATENT DOCUMENTS

| | | |
|---|---|---|
| DE | 100 50 071 A1 | 6/2001 |
| EP | 0 946 473 | 12/1997 |
| EP | 0 837 851 | 5/2002 |
| EP | 1 201 632 A1 | 5/2002 |
| EP | 1 223 210 B1 | 3/2004 |
| JP | 10-236992 | 9/1998 |
| WO | WO 01/10803 A1 | 2/2001 |
| WO | WO 02/055463 | 7/2002 |
| WO | WO 02/079344 | 10/2002 |

OTHER PUBLICATIONS

Brown et al., "Aromatic Polyfluoro-Compounds-XXXVIII 1,2,3,4-Tetrafluorodibenzofuran and Some Nucleophilic Replacement Reactions", *Tetrahedron*, vol. 23, pp. 4041-4045 (1967).
Machine English Translation of JP 10-236992 from the Japanese Patent Office.
Ichinose et al., "High Optical Anisotropy and Small Rotational Viscosity LC Mixture for Filed-Sequential Color TN-LCDs", IDW, LTC4-3, pp. 77-80 (2000).
English language abstract of EP 1 223 210 B1.

* cited by examiner

*Primary Examiner*—Shean C Wu
(74) *Attorney, Agent, or Firm*—Millen, White, Zelano & Branigan, P.C.

(57) ABSTRACT

A compound of the formula (I) is described

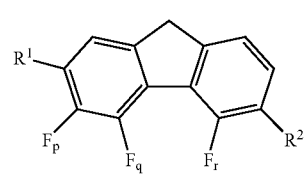

(I)

where $R^1$ and $R^2$ are defined in the specification and $p=q=r=0$ or 1 with $p+q+r\neq 0$. The compound of formula (I) has high dielectric anisotropy, thermally stable, fast response time and high voltage holding ratio, which is used as a liquid crystal medium for the liquid-crystal displays such as ECB, in-plane-switching (IPS) and VA display mode.

20 Claims, 1 Drawing Sheet

τVmin curve (T$_C$-30 K; monopolar pulse; 1.3 μm)

Response time τ [μs]

V [volts]

POLYFLUORINATED FUSED AROMATICS AND THEIR USE IN LIQUID-CRYSTAL MIXTURES

This application claims priority to German Patent Application No. 10 2004 022 914.2, filed May 13, 2004.

An ever-increasing number of applications of LCDs, for example use in automobiles, in which a temperature range of from −40° C. to 100° C. can quite possibly exist, but also portable units such as cellphones and notebook PCs, requires liquid-crystal mixtures which have firstly a very wide working temperature range and secondly a minimum threshold voltage.

There is therefore a continuing demand for novel, suitable liquid-crystal mixtures and mixture components. As described in Ichinose et al. (IDW'00, Abstr. LCT4-3) or in DE-A 100 50 071, materials are being sought in which there is coexistence of high optical anisotropy (Δn) and low rotational viscosity, although other parameters such as high absolute values of dielectric anisotropy (Δε) are likewise preferentially required, in addition to further parameters relevant to the application.

3-, 4- or 5-fluorinated fluorenes having wing groups, i.e. the alkyl and alkyloxy groups which are substantially responsible for the liquid-crystalline properties and the compatibility with other components of liquid-crystal mixtures, in the 2 and 7 positions of the particular fluorene skeletons are known from EP-A-1 223 210 and WO 01/010803 as components for liquid-crystal mixtures.

However, since the manufacturers of liquid-crystal displays have a constant interest in improved liquid-crystal mixtures, there is still a need for further components of liquid-crystal mixtures, with which individual parameters relevant to the application, for example the dielectric anisotropy (Δε) or the optical anisotropy (Δn), can be optimized.

It is therefore an object of the present invention to provide novel components for use in nematic or cholesteric or chiral-smectic liquid-crystal mixtures which have high absolute values of dielectric anisotropy combined with a favorable ratio of viscosity to clearing point. In addition, the compounds should to a high degree preferably be light- and UV-stable, and also thermally stable. In addition, they should preferably be suitable for realizing a high voltage holding ratio (VHR). In addition, they should preferably have good synthetic accessibility and therefore potentially be inexpensive.

According to the invention, these objects are achieved by compounds of the formula (I)

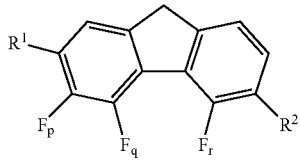
(I)

where:
$R^1$ is
a) H
b) a straight-chain or branched alkyl radical having from 1 to 16 carbon atoms or a straight-chain or branched alkenyl radical having from 2 to 16 carbon atoms, in which b1) one or more nonadjacent and nonterminal $CH_2$ groups may be replaced by —O—, —C(═O)O—, —O—C(═O)—, —O—C(═O)—O—, —C(═O)— or —Si$(CH_3)_2$— and/or b2) one $CH_2$ group may be replaced by —C≡C—, cyclopropane-1,2-diyl, cyclobutane-1,3-diyl, cyclohexane-1,4-diyl or phenylene-1,4-diyl and/or b3) one or more hydrogen atoms may be replaced by F and/or Cl c) -$M^1$-$A^1$-$R^5$ $R^2$ has the same possible definitions as specified for $R^1$, with the exception of H, but independently of the definition of $R^1$ and $R^5$ $R^5$ has the same possible definitions as specified for $R^1$, with the exception of -$M^1$-$A^1$-$R^5$, but independently of the definition of $R^1$ and $R^2$ $M^1$ is —CO—O—, —O—CO—, —$CH_2$—O—, —O—$CH_2$—, —$CF_2$—O—, —O—$CF_2$—, —CH═CH—, —CF═CF—, —C≡C—, —$CH_2$—$CH_2$—CO—O—, —O—CO—$CH_2$—$CH_2$—, —$CH_2$—$CH_2$—, —$CF_2$—$CF_2$—, —$(CH_2)_4$—, —OC(═O)CF═CF— or a single bond $A^1$ is 1,4-phenylene in which one or two hydrogen atoms may be replaced by F, Cl, CN and/or $OCF_3$ or three hydrogen atoms may be replaced by fluorine, 1,4-cyclohexylene in which one or two hydrogen atoms may be replaced by $CH_3$ and/or F, 1-cyclohexene-1,4-diyl in which one hydrogen atom may be replaced by $CH_3$ or F, pyrimidine-2,5-diyl, pyridine-2,5-diyl in which one hydrogen atom may be replaced by F, or 1,3-dioxane-2,5-diyl p, q, r are each independently 0 or 1, i.e. at the value zero, —H is present at the appropriate position instead of —F, with the proviso that:
at least one of p, q, r is 1, and by liquid-crystal mixtures comprising these compounds.

Preference is given to compounds of the formulae (Ia) to (Id)

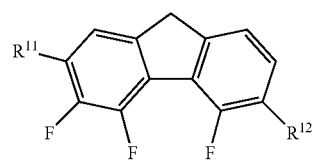
(Ia)

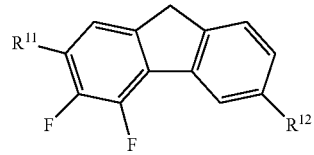
(Ib)

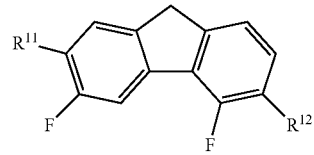
(Ic)

-continued

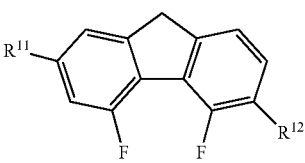
(Id)

in which:

R$^{11}$ and R$^{12}$ are each independently as specified for R$^1$ and R$^2$, preferably an alkyl or alkyloxy radical having from 1 to 10 carbon atoms or an alkenyl or alkenyloxy radical having from 2 to 10 carbon atoms, in which in each case one or more hydrogen atoms may also be replaced by F, or the R$^{15}$-A$^{15}$-M$^{15}$-moiety, with the proviso that:

R$^{11}$ and R$^{12}$ must not at the same time be R$^{15}$-A$^{15}$-M$^{15}$

R$^{15}$ is independently as specified for R$^{11}$, R$^{12}$, with the exception of R$^{15}$-A$^{15}$-M$^{15}$, preferably an alkyl or alkyloxy radical having from 1 to 10 carbon atoms or an alkenyl or alkenyloxy radical having from 2 to 10 carbon atoms A$^{15}$ is as specified for A$^1$, preferably phenylene-1,4-diyl, cyclohexane-1,4-diyl M$^{15}$ is as specified for M$^1$, preferably a single bond, —CO—O—, —O—CO—, —C≡C—, —OCF$_2$—, —CF$_2$O—, —CF$_2$CF$_2$—, —CH$_2$CH$_2$—.

Particular preference, especially for use in nematic mixtures, is given to the compounds of the formulae (Ia1), (Ia2), (Ib1) and (Ib2)

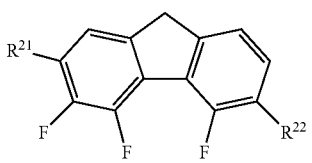
(Ia1)

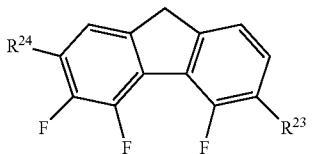
(Ia2)

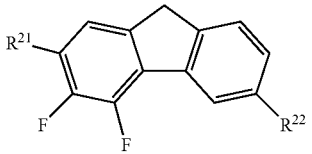
(Ib1)

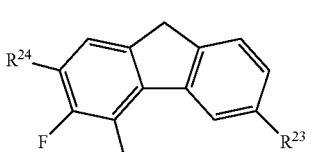
(Ib2)

in which:

R$^{21}$ and R$^{22}$ are each independently an alkyl or alkyloxy radical having from 1 to 6 carbon atoms or an alkenyl or alkenyloxy radical having from 2 to 5 carbon atoms, R$^{23}$ is an alkyl or alkyloxy radical having from 1 to 6 carbon atoms or an alkenyl or alkenyloxy radical having from 2 to 5 carbon atoms, R$^{24}$ is a R$^{15}$-A$^{15}$-M$^{15}$ moiety in which R$^{15}$ is an alkyl or alkyloxy radical having from 1 to 10 carbon atoms or an alkenyl or alkenyloxy radical having from 2 to 10 carbon atoms A$^{15}$ is phenylene-1,4-diyl, cyclohexane-1,4-diyl M$^{15}$ is a single bond or —CH$_2$CH$_2$—.

The provision of compounds of the formula (I) in a quite general sense considerably broadens the range of liquid-crystalline substances which are suitable for producing liquid-crystalline mixtures from different performance aspects.

In this context, the compounds of the formula (I) have a broad field of application. Depending on the selection of the substituents, they may be added to other classes of compound, in order, for example, to influence the dielectric and/or optical anisotropy of such a dielectric. They may also serve to optimize its threshold voltage and/or its viscosity. The compounds may also serve to increase the mesophase range or to adjust individual mesophases to parameters relevant to the application.

The compounds of the formula (I) are particularly suitable, even in small amounts in the mixture, for influencing the dielectric anisotropy (Δε) and/or the optical anisotropy Δn of liquid-crystal mixtures. The compounds of the formula (I) are particularly suitable, even in small amounts in the mixture, for reducing the response time of ferroelectric liquid-crystal mixtures. The compounds of the formula (I) are likewise particularly suitable for adjusting the broadness of the S$_C$ or N phase to application requirements. The addition of the inventive compounds can also lead to the solubility limit of fluorinated derivatives of fluorene having wing groups in the 2 and 7 positions, as described in the introduction to the description, being raised, and to the proportion of compounds having a high absolute contribution to the dielectric anisotropy thus rising.

The present invention thus provides compounds of the formula (I) and for the use of these compounds as components of liquid-crystalline mixtures and liquid-crystalline mixtures comprising one or more compounds of the formula (I).

The compounds of the formula (I) may be used in various liquid-crystal mixtures, for example chiral-smectic, nematic or cholesteric liquid-crystal mixtures. In the case of nematic mixtures, they are particularly suitable for active matrix displays (AM-LCD) (see, for example, C. Prince, Seminar Lecture Notes, Volume I, p. M-3/3-M-22, SID International Symposium 1997, B. B. Bahadur, Liquid Crystal Applications and Uses, Vol. 1, p. 410, World Scientific Publishing, 1990, E. Luder, Recent Progress of AMLCD's, Proceedings of the 15th International Display Research Conference, 1995, p. 9-12) and in-plane-switching displays (IPS-LCD), and, in the case of smectic liquid-crystal mixtures, for smectic (ferroelectric or antiferroelectric) displays. Further display possibilities are the ECB and VA display mode in the case of nematic and cholesteric LC mixtures.

Further components of liquid-crystal mixtures which comprise inventive compounds of the formula (I) are preferably selected from the known compounds having smectic and/or nematic and/or cholesteric phases. Mixture components suitable in this context are listed in particular in WO 00/36054, DE-A-195 31 165 and EP-A-0 893 424, which are explicitly incorporated herein by way of reference.

The present invention therefore also provides liquid-crystal mixtures, which comprise at least one compound of the formula (I), preferably in an amount of from 1 to 40% by weight based on the liquid-crystal mixture. The mixtures preferably comprise at least 3 further components of smectic and/or nematic and/or cholesteric phases in addition to compounds of the formula (I). The invention additionally provides electrooptical displays (liquid-crystal displays) which comprise the inventive mixtures.

Preference is given to displays which comprise the inventive nematic or smectic (ferroelectric or antiferroelectric) mixtures in combination with active matrix elements.

The inventive displays are typically constructed in such a way that one liquid-crystal layer is enclosed on both sides by layers which are typically, in this sequence starting from the LC layer, at least one alignment layer, electrodes and a boundary layer (for example of glass). In addition, they may comprise spacers, adhesive frames, polarizers and thin color filter layers for color displays. Further possible components are antireflection, passivation, compensation and barrier layers, and also electrically nonlinear elements such as thin-film transistors (TFT) and metal-insulator-metal (MIM) elements. The construction of liquid-crystal displays has already been described in detail in relevant monographs (see, for example, E. Kaneko, "Liquid Crystal TV Displays: Principles and Applications of Liquid Crystal Displays", KTK Scientific Publishers, 1987).

Examples of possible synthetic routes to compounds of the formula (I) are specified in schemes 1 to 4 which follow, although other processes are also feasible and possible.

The following abbreviations are used:
n-BuLi n-butyllithium
s-BuLi sec-butyllithium
DME 1,2-dimethoxyethane
DMF N,N-dimethylformamide
LDA lithium diisopropylamide
LICKOR n-butyllithium+potassium tert-butoxide
LITMP lithium 2,2,6,6-tetramethylpiperidide
MEK methyl ethyl ketone (2-butanone)
MTBE tert-butyl methyl ether
PCC pyridinium chlorochromate
Tf $CF_3SO_2$
TFAA trifluoroacetic anhydride
TMEDA N,N,N',N'-tetramethylethylenediamine
4-TsOH 4-toluenesulfonic acid Scheme 1

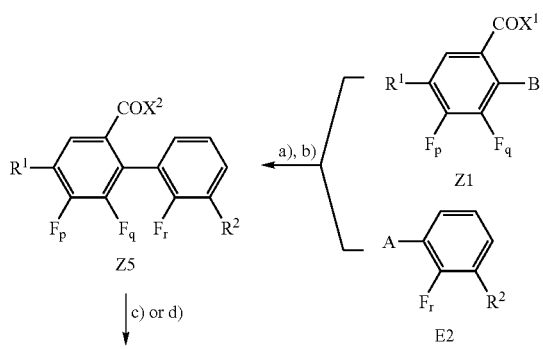

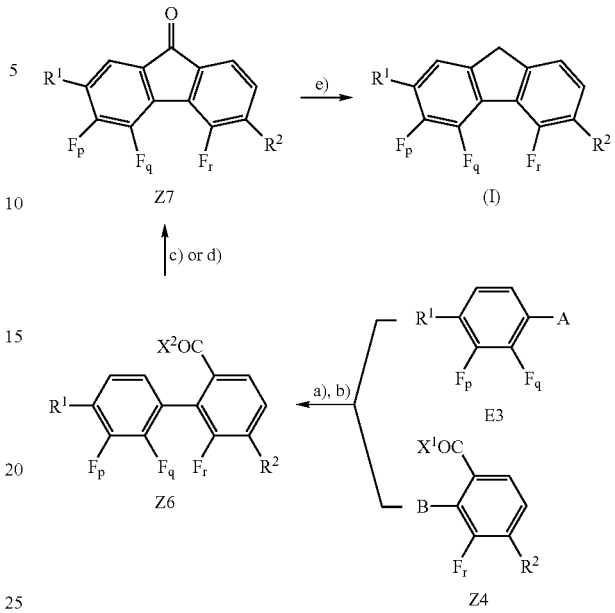

a) (in scheme 1: where $X^1$=H or $X^1$=$NR_2$; R=for example ethyl, isopropyl; A=Br, I, OTf and B=$B(OH)_2$ or A=$B(OH)_2$ and B=Br, I, OTf) Pd catalyst according to *J. Org. Chem.* 1991, 56, 1683; *Synthesis* 1998, 1195; *Can. J. Chem.* 2000, 78, 905919; *J. Chem. Soc., Perkin Trans.* 2 1999, 481; *J. Chem. Soc., Perkin Trans.* 2, 2000, 27; *J. Am. Chem. Soc.* 2000, 122, 4020; *Tetrahedron Lett.* 2001, 42, 6523; *J. Org. Chem.* 1997, 62, 8535 b) (in scheme 1: only where $X^1$=H)
$KMnO_4/H_2O$/acetone or sodium perborate/AcOH according to *Bull. Chem. Soc. Jpn.* 1986, 59, 3285; *J. Am. Chem. Soc.* 1984, 106, 3297; *Synthesis* 1993, 895; *Tetrahedron* 1989, 45, 3299 c) (in scheme 1: where X=$NR_2$; R=for example ethyl, isopropyl) LDA/THF according to *J. Org. Chem.* 1991, 56, 1683; *Synthesis* 1998, 1195 d) (in scheme 1: where $X^2$=OH)
1. $SOCl_2$ 2. $AlCl_3/CH_2Cl_2$ or $C_2H_4Cl_2$ according to *Organikum, VEB Deutscher Verlag der Wissenschaften*, 15th ed., Berlin, 1984, ch. 7.1.5.4, p. 527ff and ch. D.5.1.7.1, p. 404; WO 94/26693 or $TFAA/CHCl_3$ according to *Synthesis* 1998, 1195 e) $Et_3SiH/CF_3COOH$ according to *J. Org. Chem.* 1973, 38, 2675; *Mol. Cryst. Liq. Cryst.* 1991, 199, 327 f) 1. s-BuLi/TMEDA/THF 2. $B(OMe)_3$ 3. $H_3O^+$ according to *Bull. Korean Chem. Soc.* 1993, 14, 732; *J. Org. Chem.* 1977, 42, 1823; *J. Org. Chem.* 1991, 56, 1683; *Tetrahedron Lett.* 1985, 26, 5997 g) 1. n-BuLi 2. $C_2Br_2Cl_4$ or $Br_2$ according to *J. Chem. Soc., Perkin Trans. 1* 1995, 1265; U.S. Pat. No. 6,114,538 h) 1. $NaBH_4$/THF 2. $Me_2SO_4$ 3. $PCC/CH_2Cl_2$ according to *Org. Prep. Proceed. Int.* 1999, 31, 694

Inventive fluorenes (I) can be prepared, for example, according to scheme 1 by reduction of the corresponding 9-fluorenones Z7 which are obtainable starting from correspondingly substituted biphenyl-2-carboxamides (Z5 or Z6 where $X^2$=$NR_2$, R=for example ethyl or isopropyl) by regiospecific metalation and subsequent cyclization (according to *J. Org. Chem.* 1991, 56, 1683; *Synthesis* 1998, 1195) or starting from correspondingly substituted biphenyl-2- carboxylic acids (Z5 or Z6 where $X^2$=OH) by conversion to the carbonyl chloride and subsequent intramolecular Friedel-Crafts acylation (according to Organikum, VEB Deutscher Verlag der Wissenschaften, 15th ed., Berlin, 1984, ch. 7.1.5.4, p. 527ff and ch. D.5.1.7.1, p. 404; WO 94/26693; alternatively, the carboxylic acid may also be reacted directly according to Synthesis 1998, 1195). The regiochemistry, in some cases complementary, of these two cyclization methods (cf. Synthesis 1998, 1195) allows the selective preparation of fluorenes (I) fluorinated in different positions.

The biphenyls Z5 and Z6 can be prepared by Pd-catalyzed coupling starting from the corresponding boronic acids and aryl bromides, iodides or triflates Z1, E2, E3 or Z4 (A=Br, I, OTf and B=B(OH)$_2$ or A=B(OH)$_2$ and B=Br, I, OTf). In the case of the biphenyls Z5 and Z6 where $X^2$=NR$_2$, the corresponding benzamides (Z1 or Z4 where X=NR$_2$) are coupled. In the case of the biphenyls Z5 and Z6 where $X^2$=OH, preference is given to using the corresponding benzaldehydes (Z1 or Z4 where $X^1$=H) in the Pd-catalyzed coupling and to subsequently oxidizing the resulting biphenyl-2-carbaldehyde (Z5 or Z6 where $X^2$=H) to the carboxylic acid. Alternatively, the benzoic acids Z1 or Z4 ($X^1$=OH) may also be used in masked form as the oxazoline derivative (i.e. COX$^1$=4,4-dialkyl-4,5-dihydrooxazol-2-yl) in the Pd-catalyzed coupling; the protecting group may then be removed again, for example, by treating with acid (see Synthesis 1998, 1195; Angew. Chem. 1996, 108, 1640).

Inventive compounds of the formula (I), especially the preferred compounds of the formulae (Ia), (Ib) and (Id) can be prepared, for example, according to scheme 2 or scheme 3 via the regiospecific metalation and cyclization of biphenyl-2-carboxamides Z5a or Z6a (corresponds to Z5 or Z6 where X=NEt$_2$ in scheme 1).

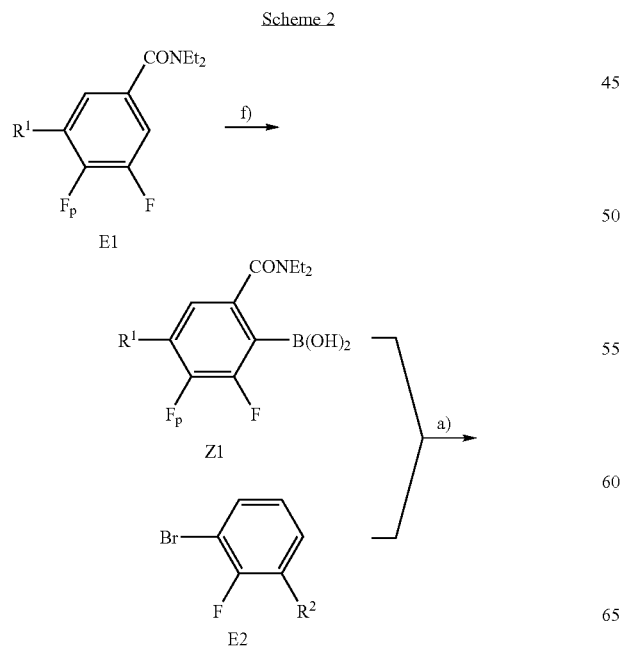

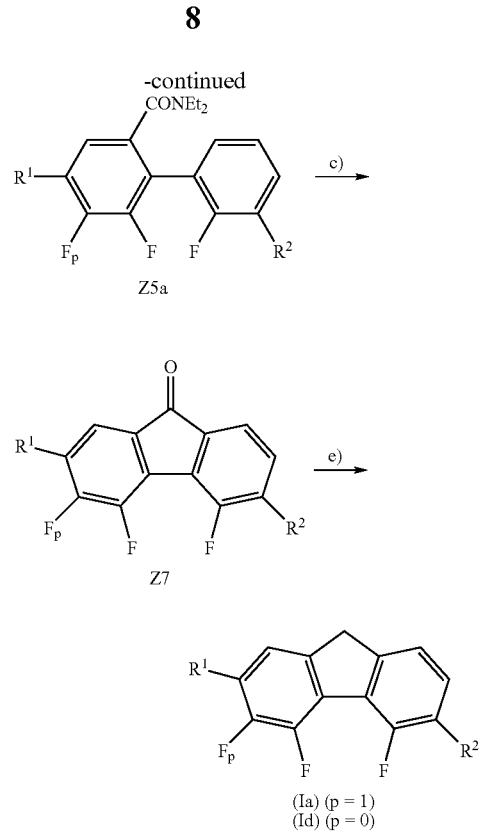

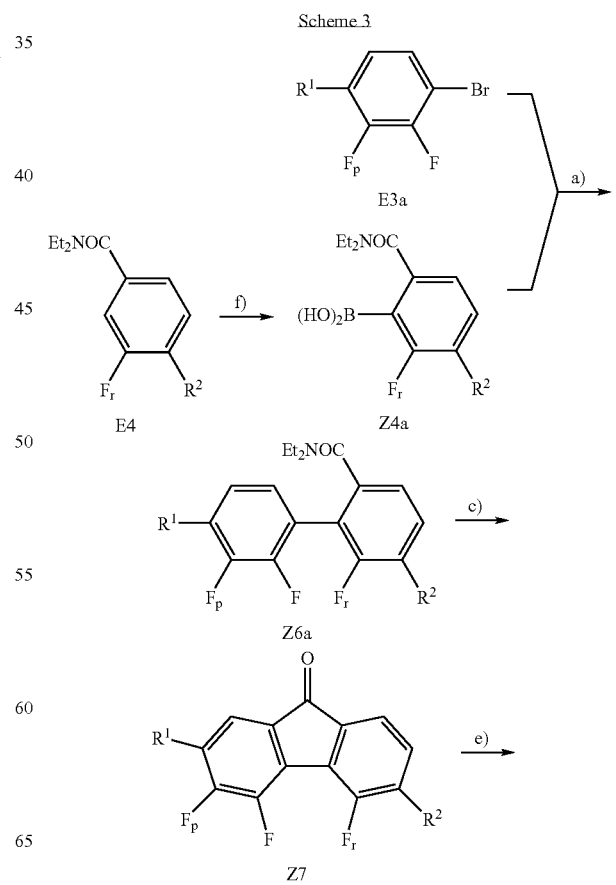

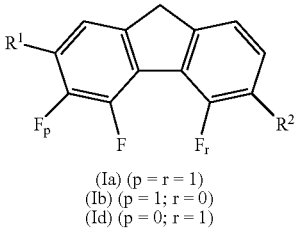

(Ia) (p = r = 1)
(Ib) (p = 1; r = 0)
(Id) (p = 0; r = 1)

Reactants E1 where $R^1$=H can be prepared from commercially available 3,4-difluorobenzoic acid [455-86-7] (where p=1) or commercially available 3-fluorobenzoic acid [455-38-9] (where p=0) by successive reaction with thionyl chloride and diethylamine (according to Organikum, VEB Deutscher Verlag der Wissenschaften, 15th ed., Berlin, 1984, ch. 7.1.5, p. 529 and 513; Bull. Korean Chem. Soc. 1993, 14, 732). Reactants E1 where p=0 and $R^1$=alkyl or alkyloxy can be obtained analogously from the corresponding 3-alkyl- or 3-alkoxy-5-fluorobenzoic acids which are obtainable in turn from the corresponding 1-alkyl- or 1-alkyloxy-3-bromo-5-fluorobenzenes by successive reaction with magnesium and carbon dioxide (according to Organikum, VEB Deutscher Verlag der Wissenschaften, 15th ed., Berlin, 1984, ch. 7.3.6, p. 623ff; alternatively, it is possible to metalate with n-BuLi and react with carbon dioxide according to J. Chem. Soc., Perkin Trans. I 1995, 2729 and GB 1,098,387). Of the 1-alkyl-3-bromo-5-fluorobenzenes required for this purpose, the methyl derivative is known from the literature [202865-83-6] and commercially available. Higher alkyl homologs can be prepared from 3-bromo-5-fluorobenzaldehyde [188813-O$_2$-7] (U.S. Pat. No. 6,028,233; U.S. Pat. No. 6,391,907) which is known from the literature by Wittig reaction with alkyltriphenylphosphonium halides (according to U.S. 20030229096) and subsequent hydrogenation (according to Mol. Cryst. Liq. Cryst. 1991, 204, 43). Of the 1-alkyloxy-3-bromo-5-fluorobenzenes, the methoxy derivative [29578-39-0] and the ethoxy derivative [212307-87-4] are known from the literature; higher homologs may be obtained, for example, from commercially available 1-bromo-3,5-difluorobenzene [461-96-1] analogously to the procedure described in WO 03/101956 for 1-bromo-3-fluoro-5-benzyloxybenzene [130722-44-0] or from 3-bromo-5-fluorophenol [433939-27-6] which is likewise described there by Williamson etherification with alkyl bromides.

The reactant E2 where $R^2$=H (1-bromo-2-fluorobenzene) [1072-85-1] is commercially available. It is possible from this to prepare reactants E2 where $R^2$=alkyl, 4-alkylcyclohexyl by metalation with LDA or LITMP (Tetrahedron Lett. 1996, 37, 6551) and subsequent, successive reaction with appropriate aldehydes or cyclohexanones, dehydration with phosphorus pentoxide or 4-TsOH (according to J. Chem. Soc., Perkin Trans II 1989, 2041; WO 96/00710; EP-B 0132377) and hydrogenation over $PtO_2$ in ethanol (according to Mol. Cryst. Liq. Cryst. 1991, 204, 43). Reactants E2 where $R^2$=alkyloxy can likewise be prepared from 1-bromo-2-fluorobenzene after metalation with LDA or LITMP by subsequent, successive reaction with trimethyl borate, acid hydrolysis, oxidation with hydrogen peroxide (according to GB 1,098,387) and Williamson etherification with appropriate alkyl bromides.

The reactants E3a (corresponding to E3 where A=Br and q=1 in scheme 1) where $R^1$=H are commercially available: 1-bromo-2,3-difluorobenzene [38573-88-5] and 1-bromo-2-fluorobenzene [1072-85-1]. Some reactants E3a where $R^1$=alkyl or alkyloxy and p=0 (4-alkyloxy-1-bromo-2-fluorobenzenes and 4-alkyl-1-bromo-2-fluorobenzenes) are described in the literature and obtainable, for example, starting from 4-bromo-3-fluorophenol [121219-03-2] by Williamson etherification with alkyl bromides or starting from purchasable 1-bromo-2-fluoro-4-iodobenzene [136434-77-0] analogously to the procedure described in WO 00/04111, Mol. Cryst Liq. Cryst. 1991, 195, 221 and ibid. 1991, 204, 43. Reactants E3a where $R^1$=4-alkylcyclohexyl and p=0 are likewise known from the literature (for example [184706-05-6], [160975-62-2]); a homologization is familiar to those skilled in the art. Reactants E3a where $R^1$=alkyl or alkyloxy and p=1 (4-alkyloxy-1-bromo-2,3-difluorobenzenes and 4-alkyl-1-bromo-2,3-fluorobenzenes) can be obtained starting from 1-alkyl-2,3-difluorobenzenes or 1-alkoxy-2,3-difluorobenzenes which are known from the literature by lithiation with n-BuLi (J. Chem. Soc., Perkin Trans II 1989, 2041) and subsequent reaction with 1,2-dibromotetrachloroethane or bromine (according to J. Chem. Soc., Perkin Trans. 11995, 1265; U.S. Pat. No. 6,114,538).

Reactants E4 where r=0 are either commercially available (N,N-diethyl-benzamide [1696-17-9]) or can be prepared starting from commercially available 4-alkyl- or 4-alkyloxy-benzoic acids or 4-(4'-alkylcyclohexyl)-benzoic acids which are familiar to those skilled in the art (Angew. Chem. Int. Ed. Engl. 1977, 16, 100) by successive reaction with thionyl chloride and diethylamine (according to Organikum, VEB Deutscher Verlag der Wissenschaften, 15th ed., Berlin, 1984, ch. 7.1.5, p. 529 and 513; Bull. Korean Chem. Soc. 1993, 14, 732). The reactant E4 where r=1 and $R^2$=H can be prepared analogously from commercially available 3-fluorobenzoic acid [455-38-9]. Reactants E4 where r=1 and $R^2$=alkyl or alkyloxy can be obtained analogously from the corresponding 4-alkyl- or 4-alkoxy-3-fluorobenzoic acids which are obtainable in turn from the corresponding 1-alkyl- or 1-alkyloxy-4-bromo-2-fluorobenzenes by successive reaction with magnesium and carbon dioxide (according to Organikum, VEB Deutscher Verlag der Wissenschaften, 15th ed., Berlin, 1984, ch. 7.3.6, p. 623ff; alternatively, it is possible to metalate with n-BuLi and react with carbon dioxide according to J. Chem. Soc., Perkin Trans. I 1995, 2729 and GB 1,098,387). Some of the 1-alkyl- and 1-alkyloxy-4-bromo-2-fluorobenzenes required for this purpose are known from the literature and can be prepared, for example, from commercially available 1-bromo-3-fluoro-4-iodobenzene [105931-73-5] or from commercially available 4-bromo-2-fluorophenol [2105-94-4] analogously to the procedure described in WO 00/04111 and Mol. Cryst Liq. Cryst. 1991, 195, 221.

Inventive compounds of the formula (I), particularly compounds of the formula (I) where p=1, especially the preferred compounds of the formulae (Ia), (Ib) and (Ic) can be prepared, for example, according to scheme 4, via the intramolecular Friedel-Crafts acylation of the corresponding biphenyl-2-carboxylic acids Z6b (corresponding to Z6 where X=OH in scheme 1) or their carbonyl chlorides.

The preparation of reactants E3b (corresponding to E3 where A=B(OH)$_2$ and p=1 in scheme 1) where $R^1$=H, alkyl, alkyloxy is described in the literature, and a homologization is familiar to those skilled in the art (for example J. Chem. Soc., Perkin Trans 111989, 2041; WO 00/04111).

The reactants E5 in scheme 4 also serve as starting materials for the synthesis of the reactants E4 in scheme 3, and their availability and their synthesis have already been described there.

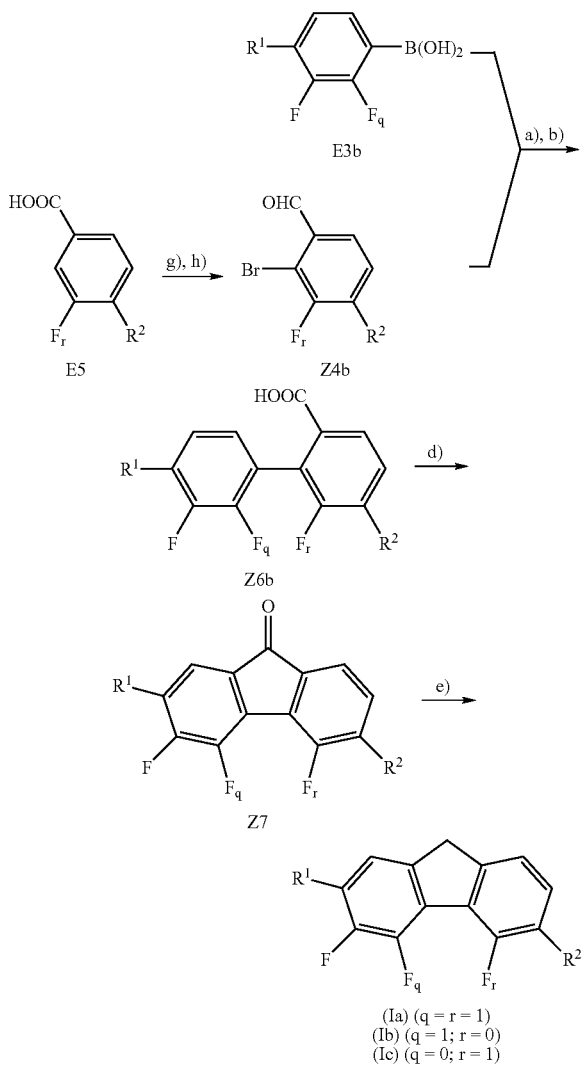

In inventive compounds of the formula (I) where $R^1$=H and $R^2 \neq$H and p=q=1 and compounds of the formula (I) where $R^2$=H and $R^1 \neq$H and r=1 or p=q=r=1, it is possible to introduce alkyl or alkyloxy substituents into the 2 or 6 position of the fluorine skeleton after metalation in the 2 or 6 position of the fluorine skeleton (i.e. in each case in the single H-substituted ortho-position to one of the fluorene substituents present) with LICKOR by reaction with alkyl bromides (according to Recl. Trav. Chim. Pays-Bas 1994, 113, 529; Synth. Commun. 1990, 20, 1701) or with n-BuLi or s-BuLi, reaction with trimethyl borate, acid hydrolysis and oxidation with hydrogen peroxide (according to J. Chem. Soc., Perkin Trans. 2, 1989, 2041; ibid. 1999, 481). Substituents $R^1$ or $R^2$ with further definitions specified above can be introduced correspondingly after metalation analogously to the procedure described in DE-A 101 01 022 (see, for example, schemes 4, 5, 6 and 7).

The invention is illustrated in detail by the examples which follow.

EXAMPLE 1

3,4-Difluoro-6-propylfluorene

[Compound (I) where p=q=1; r=0; $R^1$=H; $R^2$=$C_3H_7$]

a) A solution of 77 ml of TMEDA in 1.4 l of dry THF is cooled to −70° C., and 365 ml of s-BuLi (1.4 M solution in cyclohexane) are added dropwise under a protective gas atmosphere. The mixture is stirred for a further 15 min and a solution of 107 g of N,N-diethyl-4-n-propylbenzamide (prepared from purchasable 4-n-propylbenzoyl chloride [52710-27-7] by reaction with diethylamine) in 0.9 l of THF is subsequently added in such a way that the internal temperature always remains below −70° C. Subsequently, the mixture is stirred for a further 2 h and then 109 ml of trimethyl borate are added dropwise at the same temperature. The reaction mixture is allowed to come slowly to −10° C., and admixed with 400 ml of saturated ammonium chloride solution and acidified to pH 5-6 with hydrochloric acid. After extraction with MTBE, the combined organic phases are washed with saturated NaCl solution and dried over sodium sulfate. The crude 2-diethyl-carbamoyl-5-propylphenylboronic acid obtained after the removal of the solvent is dissolved without further purification in a mixture of 625 ml of DME and 100 ml of ethanol, and added to a mixture of 60.4 g of 1-bromo-2,3-difluorobenzene and 14.5 g of tetrakis(triphenylphosphine)palladium(0) in 780 ml of DME. After a solution of 199 g of sodium carbonate in 940 ml of water has been added, the mixture is heated to boiling for 4 h. The slightly cooled phases are separated, the aqueous phase is extracted with MTBE, and the combined organic phases are washed with saturated NaCl solution and dried over sodium sulfate. After the solvents have been removed under reduced pressure, the crude product is chromatographed on silica gel using 85:15 (v/v) heptane/ethyl acetate as the eluent. The resulting N,N-diethyl-2',3'-difluoro-5-propylbiphenyl-2-carboxamide is dissolved in 375 ml of dry THF and added dropwise to a solution, cooled to from −30 to −40° C., of LDA, prepared from 54 ml of diisopropylamine and 240 ml of n-BuLi (1.6 M solution in hexane), in 250 ml of THF. The mixture is stirred for a further 3 h and subsequently quenched with saturated ammonium chloride solution. The reaction mixture is allowed to come to 0° C. and acidified with hydrochloric acid. After extraction with MTBE, the combined organic phases are washed with 5 percent sodium hydrogen-carbonate solution and saturated NaCl solution, and dried over sodium sulfate. After the solvent has been removed under reduced pressure, the residue is worked up chromatographically on silica gel using 9:1 (v/v) heptane/ethyl acetate as the eluent. The product-containing fractions are combined, the eluent is removed under reduced pressure and the residue is dissolved with exclusion of moisture in 300 ml of trifluoroacetic acid. 30 ml of triethylsilane are slowly added dropwise at room temperature and the mixture is subsequently stirred at this temperature for 2 h and at 40-70° C. for 4 h. After cooling, the reaction mixture is added to water and extracted with dichloromethane. The combined organic extracts are washed with 5 percent sodium hydrogencarbonate solution and saturated NaCl solution, and dried over sodium sulfate. After the solvent has been removed under reduced pressure, the yellow residue is purified chromatographically on silica gel using heptane as the eluent and recrystallized from heptane. 7.2 g of 3,4-difluoro-6-propylfluorene are obtained.

EXAMPLE 2

2-Butyloxy-3,4-difluoro-6-propylfluorene

[Compound (I) where p=q=1; r=0; $R^1$=OC$_4$H$_9$; $R^2$=C$_3$H$_7$]

A solution of 5.2 g of 3,4-difluoro-6-propylfluorene (example 1) in 50 ml of dry THF is cooled to −70° C. and 15 ml of n-BuLi (1.6 m solution in hexane) are added dropwise under a protective gas atmosphere in such a way that the internal temperature is always below −70° C. Subsequently, the mixture is stirred at this temperature for a further 2 h and then 2.7 g of trimethyl borate dissolved in 10 ml of THF are added at the same temperature. The reaction mixture is allowed to come to −10° C., quenched with water and acidified with hydrochloric acid. After extraction with MTBE, the combined organic phases are washed with saturated NaCl solution and dried over sodium sulfate. The crude boronic acid obtained after the removal of the solvent is dissolved in 100 ml of MTBE, heated to boiling, admixed rapidly with 7.5 ml of 35 percent aqueous hydrogen peroxide solution and stirred under reflux for a further 2.5 h. After cooling, the phases are separated, the aqueous phase is extracted once more with MTBE and the combined organic phases are washed successively with water, saturated sodium sulfite solution and saturated NaCl solution. After drying over sodium sulfate and removal of the solvent under reduced pressure, the crude product is purified by column chromatography on silica gel using 9:1 (v/v) heptane/ethyl acetate as the eluent. The resulting 3,4-difluoro-6-propylfluoren-2-ol is heated to boiling with 2.4 g of 1-bromobutane and 5.4 g of potassium carbonate in 120 ml of MEK for 6 h. After cooling, the reaction mixture is added to ice/water and extracted with MTBE, and the organic phases are washed with water and saturated NaCl solution and dried over sodium sulfate. After the solvents have been removed under reduced pressure, the colorless crude product is purified chromatographically on silica gel with 2:8 (v/v) dichloromethane/heptane as the eluent and recrystallized from heptane. 2.7 g of 2-butyloxy-3,4-difluoro-6-propylfluorene are obtained.

EXAMPLE 3

3,4-Difluoro-2,6-dipropylfluorene

[Compound (I) where p=q=1; r=0; $R^1$=$R^2$=C$_3$H$_7$]

Analogously to example 1, using 1-bromo-2,3-difluoro-4-propylbenzene [prepared from 1,2-difluoro-3-propylbenzene by lithiation with n-BuLi in THF at −70° C. and subsequent reaction with bromine] instead of 1-bromo-2,3-difluorobenzene, 3,4-difluoro-2,6-dipropylfluorene is obtained.

EXAMPLE 4

3,4,5-Trifluoro-6-propylfluorene

[Compound (I) where p=q=r=1; $R^1$=H; $R^2$=C$_3$H$_7$]

Analogously to example 1, but using N,N-diethyl-3,4-difluorobenzamide (prepared from purchasable 3,4-difluorobenzoic acid [455-86-7] by successive reaction with thionyl chloride and diethylamine) instead of N,N-diethyl-4-n-propylbenzamide and 1-bromo-2-fluoro-3-propylbenzene (prepared from 1-bromo-2-fluorobenzene by lithiation with LDA in THF at −70° C. and subsequent reaction with DMF, Wittig reaction of the resulting 3-bromo-2-fluorobenzaldehyde with ethyltriphenylphosphonium bromide and potassium tert-butoxide in THF and hydrogenation with platinum oxide in ethanol) instead of 1-bromo-2,3-difluorobenzene, 3,4,5-trifluoro-6-propylfluorene is obtained.

EXAMPLE 5

2-Butyloxy-3,4,5-trifluoro-6-propylfluorene

[Compound (I) where p=q=r=1; $R^1$=OC$_4$H$_9$; $R^2$=C$_3$H$_7$]

Analogously to example 2, but using 3,4,5-trifluoro-6-propylfluorene (example 4) instead of 3,4-difluoro-6-propylfluorene (example 1), 2-butyloxy-3,4,5-trifluoro-6-propylfluorene is obtained.

Use Example 1

A chiral-smectic C mixture consisting of

| | |
|---|---|
| 2-(4-Heptyloxyphenyl)-5-nonylpyrimidine | 19.6% |
| 5-Nonyl-2-(4-octyloxyphenyl)pyrimidine | 19.6% |
| 5-Nonyl-2-(4-nonyloxyphenyl)pyrimidine | 19.6% |
| 2-(2,3-Difluoro-4-heptyloxyphenyl)-5-nonylpyrimidine | 6.5% |
| 2-(2,3-Difluoro-4-octyloxyphenyl)-5-nonylpyrimidine | 6.5% |
| 2-(2,3-Difluoro-4-nonyloxyphenyl)-5-nonylpyrimidine | 6.5% |
| 5-Hexyloxy-2-(4-hexyloxyphenyl)pyrimidine | 19.6% |
| (S)-4-[4'-(2-Fluorooctyloxy)biphenyl-4-yl]-1-heptylcyclo-hexanecarbonitrile | 2.0% | is admixed with 5% of the compound from example 2. This results in a mixture which, as demonstrated by FIG. 1, is suitable for the operation of displays in inverse mode, since the curve profile has the required minimum and the values lie within the technically relevant range.

Figure 1:
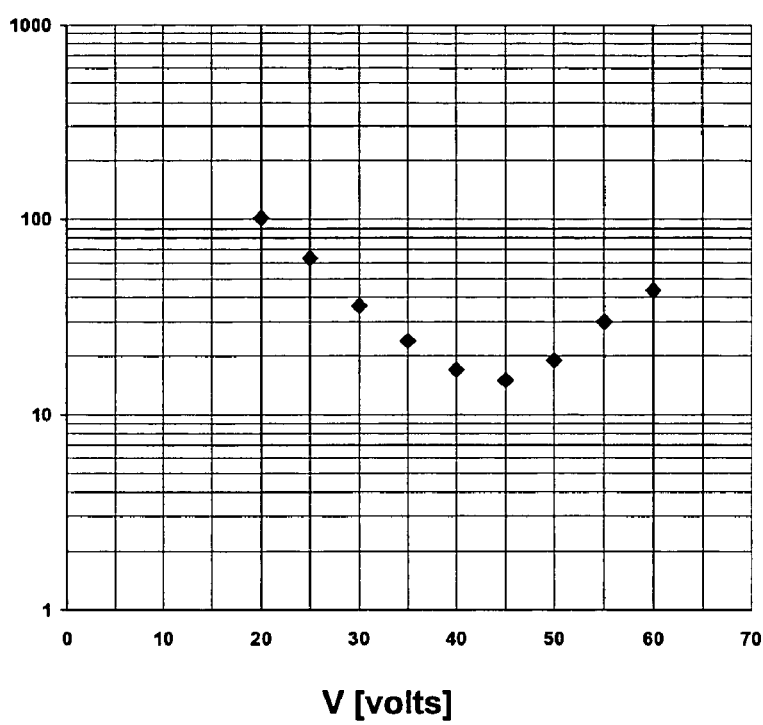
FIG. 1 shows the τVmin curve (τ plotted against the voltage) at $T_C$-30 K, monopolar pulses and a cell separation of 1.3 μm

What is claimed is:
1. A compound of formula (I)

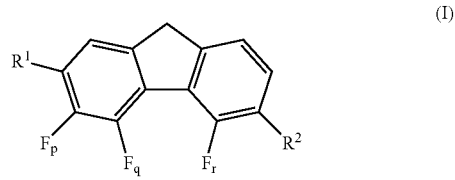

wherein
$R^1$ is
a) H,
b) a straight-chain or branched alkyl radical having 1 to 16 carbon atoms or a straight-chain or branched alkenyl radical having 2 to 16 carbon atoms, in which
b1) one or more nonadjacent and nonterminal CH$_2$ groups may be replaced by —O—, —C(=O)O—, —O—C(=O)—, —O—C(=O)—O—, —C(=O)— or —Si(CH$_3$)$_2$— and/or b2) one CH$_2$ group may be replaced by —C≡C—, cyclopropane-1,2-diyl, cyclobutane-1,3-diyl, cyclohexane-1,4-diyl or phenylene-1,4-diyl and/or b3) one or more hydrogen atoms may be replaced by F and/or Cl, or c) -M$^1$-A$^1$-R$^5$, R$^2$ is b) a straight-chain or branched alkyl radical having 1 to 16 carbon atoms or a straight-chain or branched alkenyl radical having 2 to 16 carbon atoms, in which b1) one or more nonadjacent and nonterminal CH$_2$ groups may be replaced by —O—, —C(=O)O—, —O—C(=O)—, —O—C(=O)—O—, —C(=O)— or —Si(CH$_3$)$_2$— and/or b2) one CH$_2$ group may be replaced by —C≡C—, cyclopropane-1,2-diyl, cyclobutane-1,3-diyl, cyclohexane-1,4-diyl or phenylene-1,4-diyl and/or b3) one or more hydrogen atoms may be replaced by F and/or Cl, or c) -M$^1$-A$^1$-R$^5$, R$^5$ is a) H, or b) a straight-chain or branched alkyl radical having 1 to 16 carbon atoms or a straight-chain or branched alkenyl radical having 2 to 16 carbon atoms, in which b1) one or more nonadjacent and nonterminal CH$_2$ groups may be replaced by —O—, —C(=O)O—, —O—C(=O)—, —O—C(=O)—O—, —C(=O)— or —Si(CH$_3$)$_2$— and/or b2) one CH$_2$ group may be replaced by —C≡C—, cyclopropane-1,2-diyl, cyclobutane-1,3-diyl, cyclohexane-1,4-diyl or phenylene-1,4-diyl and/or b3) one or more hydrogen atoms may be replaced by F and/or Cl, M$^1$ is —CO—O—, —O—CO—, —CH$_2$—O—, —O—CH$_2$—, —CF$_2$—O—, —O—CF$_2$—, —CH=CH—, —CF=CF—, —C≡C—, —CH$_2$—CH$_2$—CO—O—, —O—CO—CH$_2$—CH$_2$—, —CH$_2$—CH$_2$—, —CF$_2$—CF$_2$—, —(CH$_2$)$_4$—, —OC(=O)CF=CF— or a single bond A$^1$ is 1,4-phenylene in which one or two hydrogen atoms may be replaced by F, Cl, CN and/or OCF$_3$ or three hydrogen atoms may be replaced by fluorine, 1,4-cyclohexylene in which one or two hydrogen atoms may be replaced by CH$_3$ and/or F, 1-cyclohexene-1,4-diyl in which one hydrogen atom may be replaced by CH$_3$ or F, pyrimidine-2,5-diyl, pyridine-2,5-diyl in which one hydrogen atom may be replaced by F, or 1,3-dioxane-2,5-diyl, p, q, r are, each independently, 0 or 1, wherein at the value zero, —H is present at the appropriate position instead of —F, with the proviso that:

at least one of p, q, r is 1.

2. A compound as claimed in claim 1, which is of formula (Ia1), (Ia2), (Ib1) or (Ib2)

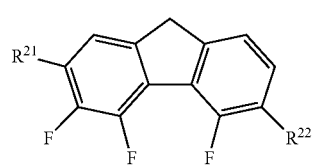
(Ia1)

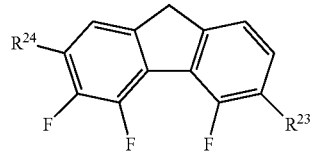
(Ia2)

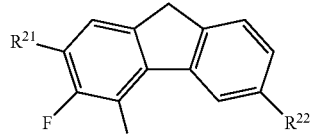
(Ib1)

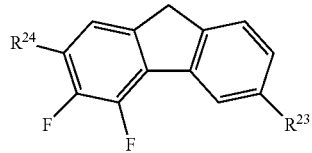
(Ib2)

wherein

R$^{21}$ and R$^{22}$ are each independently an alkyl or alkyloxy radical having 1 to 6 carbon atoms or an alkenyl or alkenyloxy radical having 2 to 5 carbon atoms, R$^{23}$ is an alkyl or alkyloxy radical having 1 to 6 carbon atoms or an alkenyl or alkenyloxy radical having 2 to 5 carbon atoms, R$^{24}$ is R$^{15}$-A$^{15}$-M$^{15}$, R$^{15}$ is an alkyl or alkyloxy radical having 1 to 10 carbon atoms or an alkenyl or alkenyloxy radical having 2 to 10 carbon atoms, A$^{15}$ is phenylene-1,4-diyl, or cyclohexane-1,4-diyl, and M$^{15}$ is a single bond or —CH$_2$CH$_2$—.

3. A liquid-crystal mixture, comprising one or more compounds of formula (I) as claimed in claim 1.

4. A liquid-crystal mixture as claimed in claim 3, which comprises one or more compounds of formula (I) in an amount of 1 to 40% by weight based on the liquid-crystal mixture.

5. A liquid-crystal mixture as claimed in claim 3, which comprises at least three further components of smectic and/or nematic and/or cholesteric phases.

6. A liquid-crystal mixture as claimed in claim 3, which is chiral-smectic.

7. A liquid-crystal mixture as claimed in claim 3, which is nematic or cholesteric.

8. A liquid-crystal display comprising a liquid-crystal mixture as claimed in claim 3.

9. A liquid-crystal display as claimed in claim 8, which is operated in ECB, IPS or VA display mode and comprises a nematic or cholesteric liquid-crystal mixture.

10. A liquid-crystal mixture, comprising one or more compounds of claim 2.

11. A liquid-crystal display comprising a liquid-crystal mixture as claimed in claim 10.

12. A compound as claimed in claim 1, which is of formula (Ia1) or (Ia2)

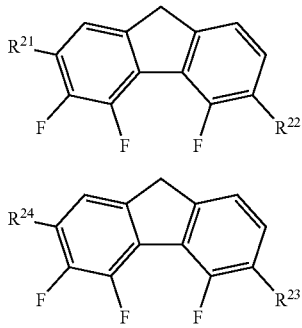

wherein
- $R^{21}$ and $R^{22}$ are each independently an alkyl or alkyloxy radical having 1 to 6 carbon atoms or an alkenyl or alkenyloxy radical having 2 to 5 carbon atoms,
- $R^{23}$ is an alkyl or alkyloxy radical having 1 to 6 carbon atoms or an alkenyl or alkenyloxy radical having 2 to 5 carbon atoms,
- $R^{24}$ is $R^{15}\text{-}A^{15}\text{-}M^{15}$,
- $R^{15}$ is an alkyl or alkyloxy radical having 1 to 10 carbon atoms or an alkenyl or alkenyloxy radical having 2 to 10 carbon atoms,
- $A^{15}$ is phenylene-1,4-diyl, or cyclohexane-1,4-diyl, and
- $M^{15}$ is a single bond or —CH$_2$CH$_2$—.

13. A liquid-crystal mixture, comprising one or more compounds of claim 12.

14. A liquid-crystal display comprising a liquid-crystal mixture as claimed in claim 13.

15. A compound as claimed in claim 1, which is 3,4-Difluoro-6-propylfluorene; 2-Butyloxy-3,4-difluoro-6-propylfluorene; 3,4-Difluoro-2,6-dipropylfluorene; 3,4,5-Trifluoro-6-propylfluorene; or 2-Butyloxy-3,4,5-trifluoro-6-propylfluorene.

16. A liquid-crystal mixture, comprising one or more compounds of claim 15.

17. A liquid-crystal display comprising a liquid-crystal mixture as claimed in claim 16.

18. A compound as claimed in claim 1, wherein
$R^2$ is
b) a straight-chain or branched alkyl radical having 1 to 16 carbon atoms or a straight-chain or branched alkenyl radical having 2 to 16 carbon atoms, in which
  b1) one or more nonadjacent and nonterminal CH$_2$ groups may be replaced by —O—, —C(=O)O—, —O—C(=O)—, —O—C(=O)—O—, —C(=O)— or —Si(CH$_3$)$_2$— and/or
  b2) one CH$_2$ group may be replaced by —C≡C—, cyclopropane-1,2-diyl, cyclobutane-1,3-diyl, cyclohexane-1,4-diyl or phenylene-1,4-diyl and/or
  b3) one or more hydrogen atoms may be replaced by F and/or Cl.

19. A liquid-crystal mixture, comprising one or more compounds of claim 18.

20. A liquid-crystal display comprising a liquid-crystal mixture as claimed in claim 19.

\* \* \* \* \*